(12) United States Patent
Derici et al.

(10) Patent No.: US 7,611,698 B2
(45) Date of Patent: Nov. 3, 2009

(54) HAIR CONDITIONING COMPOSITIONS

(75) Inventors: Leo Derici, Wirral (GB); Paul David Jenkins, Wirral (GB); Andrew Malcolm Murray, Wirral (GB); Neil Scott Shaw, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 357 days.

(21) Appl. No.: 10/514,219

(22) PCT Filed: Apr. 23, 2003

(86) PCT No.: PCT/EP03/04237

§ 371 (c)(1), (2), (4) Date: Nov. 10, 2004

(87) PCT Pub. No.: WO03/094875

PCT Pub. Date: Nov. 20, 2003

(65) Prior Publication Data

US 2005/0169864 A1    Aug. 4, 2005

(30) Foreign Application Priority Data

May 10, 2002    (GB)    ................... 0210791.0

(51) Int. Cl.
  A61K 8/73    (2006.01)
(52) U.S. Cl. .................................... 424/70.17
(58) Field of Classification Search .............. None
  See application file for complete search history.

(56) References Cited

U.S. PATENT DOCUMENTS

| | | | |
|---|---|---|---|
| 3,753,916 A | 8/1973 | Parran, Jr. | |
| 4,183,917 A | 1/1980 | Iwao et al. ................ | 424/70 |
| 5,100,657 A | 3/1992 | Ansher-Jackson et al. | |
| 5,194,639 A | 3/1993 | Connor et al. ............ | 554/66 |
| 5,589,177 A | 12/1996 | Herb et al. ................ | 424/401 |
| 5,641,480 A * | 6/1997 | Vermeer ................... | 424/70.24 |
| 5,648,323 A * | 7/1997 | Coffindaffer et al. ...... | 510/122 |
| 5,662,892 A | 9/1997 | Bolich, Jr. et al. | |
| 5,709,847 A | 1/1998 | Bissett et al. ............. | 424/59 |
| 5,733,536 A * | 3/1998 | Hill et al. ................ | 424/70.12 |
| 5,837,661 A | 11/1998 | Evans et al. | |
| 5,942,216 A | 8/1999 | Herb et al. | |
| 5,942,479 A * | 8/1999 | Frankenbach et al. ...... | 510/159 |
| 5,965,115 A | 10/1999 | Bolich, Jr. et al. ........ | 424/70.12 |
| 5,968,286 A | 10/1999 | Crudele et al. | |
| 5,985,295 A | 11/1999 | Peffly | |
| 6,017,860 A | 1/2000 | Sajic et al. | |
| 6,030,630 A | 2/2000 | Fleury et al. | |
| 6,056,946 A | 5/2000 | Crudele et al. | |
| 6,150,313 A | 11/2000 | Harmalker et al. | |
| 2001/0027171 A1 | 10/2001 | Sajac et al. | |
| 2003/0138465 A9 * | 7/2003 | Douin et al. .............. | 424/401 |

FOREIGN PATENT DOCUMENTS

| | | |
|---|---|---|
| EP | 0 455 185 | 11/1991 |
| EP | 0 530 974 | 7/1995 |
| EP | 0 715842 A2 | 6/1996 |
| WO | 92/06154 | 4/1992 |
| WO | 92/14440 | 9/1992 |
| WO | 96/17590 | 6/1996 |
| WO | 96/17592 | 6/1996 |
| WO | 97/14405 | 4/1997 |
| WO | 98/05005 | 11/1998 |
| WO | 98/50005 | 11/1998 |
| WO | 00/51550 | 9/2000 |
| WO | 03/094874 | 11/2003 |

OTHER PUBLICATIONS

GB Search Report in GB application GB 0228879.3.
GB Search Report in GB application GB 0228880.1.
Co-pending Application: Applicant: Derici et al., U.S. Appl. No. 10/538,188, filed Jun. 9, 2005.
PCT International Search Report in PCT application PCT/EP 03/12220.
GB Search Report in GB application GB 0228879.0.
Yang et al., "Phase Behavior of ethylene oxide-dimethylsiloxane PEO-PDMS-PEO riblock copolymers with water"; Colloid Polymer Science; vol. 270; No. 11 (1992); pp. 1080-1084.

* cited by examiner

Primary Examiner—M P Woodward
Assistant Examiner—Bethany Barham
(74) Attorney, Agent, or Firm—Karen E. Klumas

(57) ABSTRACT

An aqueous hair conditioning composition comprising discrete, dispersed droplets of a hydrophobic conditioning oil with a mean droplet diameter (D3,2) of 4 micrometers or less, a cationic deposition polymer and a block copolymer of ethylene glycol and propylene glycol according to the Formula (I) with the mean value of y from 10 to 60 and the values of x and z both from 1 to 150, or a block copolymer according to Formula (II) wherein the mean value of a is 2 or more and the mean value of b is 2 or more.

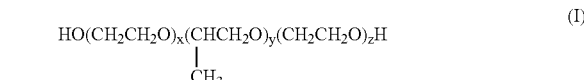

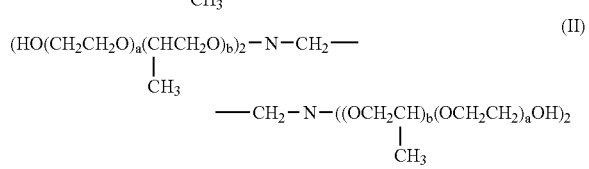

20 Claims, No Drawings

HAIR CONDITIONING COMPOSITIONS

TECHNICAL FIELD

The invention is concerned with rinse-off hair-conditioning compositions which are applied to the hair or body and then substantially rinsed away. It is particularly concerned with hair shampoo compositions and shower gels, which both clean the hair and provide conditioning benefit to the hair. More specifically, it is concerned with improving the deposition of conditioning oil onto the tip region of hair from shampoo compositions which contain dispersed hydrophobic conditioning oil droplets.

BACKGROUND AND PRIOR ART

Compositions which provide a combination of cleansing and conditioning to the hair are well know in the art. Such shampoo or shower-gel compositions typically comprise one or more surfactants for shampooing or cleansing purposes and one or more conditioning agents. The purpose of the conditioning agent is to make the hair easier to comb when wet and more manageable when dry, e.g. less static and flyaway. Typically, these conditioning agents are water-insoluble oily materials, cationic polymers or cationic surfactants.

Amongst the most popular conditioning agents used in shampoo products are oily materials such as mineral oils, naturally occurring oils such as triglycerides and silicone polymers. These are generally present in the shampoo as dispersed hydrophobic emulsion droplets. Conditioning is achieved by the oily material being deposited onto the hair resulting in the formation of a film.

Conditioning compositions which provide conditioning only, without cleansing surfactants, are also well known in the art. Such compositions are generally applied to the hair after the cleansing composition has been rinsed away.

Two methods are commonly used to enhance the deposition of conditioning oil droplets onto the hair.

One method is to use large droplets of oil, typically greater than 5 micrometers in diameter, typically with a viscosity in the range 5 to 500 Pa·s (measured at 25° C. and 21 s⁻). This method relies on physical contact between the hair and the droplets followed by the oil droplet wetting the hair surface and spreading.

Natural oils secreted by the sebaceous gland at the base of the hair lead to hair being more hydrophobic near the root rather than near the tip. This means that droplets deposited onto hair by the above methods are more likely to spread and form films on the hair at the base of the hair rather than near the tip of the hair, and this is found in practice.

Another method to enhance deposition of the conditioning oil droplets onto the hair, when the mean conditioning oil droplet size ($D_{3,2}$) is less than 2 micrometers, is to employ a cationic deposition polymer in the composition. The use of such polymers is known in the prior art.

U.S. Pat. No. 3,753,916 discloses the use of cationic polymers as deposition aids.

The use of cationic polymers means that the oil droplets are flocculated with the cationic polymer on dilution of the shampoo when the hair is rinsed. This leads to indiscriminate deposition of the cationic polymer, conditioning oil and any other insoluble materials onto the hair. There is no specific targeting of the root or the tip regions of the hair. The presence of extraneous materials in addition to the conditioning oil can lead to dulling of the appearance of the hair (loss of shine) and also to a heavy feel to the hair (because of the presence of the cationic polymer).

Certain consumers find the effects arising from the two deposition methods described above to be undesirable in that they lead to the hair feeling greasy at the roots or heavy and dull.

In attempts to overcome these problems in the prior art, it has been considered desirable to target the deposition of the conditioning oil droplets onto the tip regions of the hair in preference to the root regions, and much research has been carried out in this field of work. Although it would be desirable to make the surface of the oil droplets more hydrophilic, it had always been considered that the high levels of surfactant in shampoo compositions would dominate the surface chemistry and hydrophilicity of the oil droplets. Thus the conventional view is that irrespective of additives added to the conditioning oil droplets, the shampoo surfactant would control the droplet hydrophilicity and deposition.

It has now surprisingly been found, that by combining certain types of surface active polymer with the small conditioning oil emulsion droplets in compositions also containing cationic deposition polymers, enhanced deposition of the droplets onto the tip regions of hairs can be achieved.

The surface active polymers required to provide this selective conditioning benefit are certain block copolymers of ethylene glycol and propylene glycol

DETAILED DESCRIPTION OF THE INVENTION

In one aspect, the invention is concerned with an aqueous hair conditioning composition comprising
a) discrete, dispersed droplets of a hydrophobic conditioning oil with a mean droplet diameter ($D_{3,2}$) of 4 micrometers or less,
b) a cationic deposition polymer and
c) a block copolymer, comprising polyethyleneoxide and polypropyleneoxide blocks selected from the group consisting of (i) poloxamers according to formula I:

I:
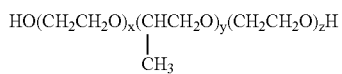

wherein the mean value of y is from 10 to 60 and the mean values of x and z are both from 1 to 150.

and (ii) poloxamines according to formula II:

II:
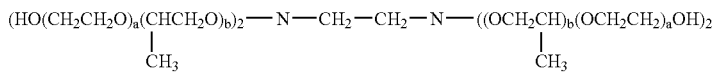

wherein the mean value of a is 2 or more and the mean value of b is 2 or more. Mixtures of the block copolymers (I) and (II) are also suitable.

Aqueous Conditioning Composition

By aqueous conditioning composition is meant a composition which has water or an aqueous solution or a lyotropic liquid crystalline phase as its major component. Suitably, the composition will comprise from 50% to 98% by weight of water, preferably from 60% to 90%.

Block Copolymer of Ethylene Glycol and Propylene Glycol.

An essential component of compositions according to the invention is a surface active block copolymer. This is a block copolymer based on polyethyleneoxide (EO) and polypropyleneoxide (PO) blocks.

A suitable block copolymer for compositions according to the invention is a copolymer of ethylene glycol and propylene glycol according to the formula I:

I:

$$HO(CH_2CH_2O)_x(CHCH_2O)_y(CH_2CH_2O)_zH$$
$$\quad\quad\quad\quad\quad\quad\quad |$$
$$\quad\quad\quad\quad\quad\quad\quad CH_3$$

wherein the mean value of y is from 10 to 60 and the mean values of x and z are both from 1 to 150.

Such copolymers have the CTFA designation "Poloxamer" and are available commercially from BASF under the trade name Pluronic (Registered Trade Mark).

It is preferred if the mean values of x and z are approximately the same value. In a more preferred version of the polymer, the values of x and z are both 20 or less. It is also preferred if the value of y is 40 or less, more preferably 20 or less.

Another suitable block copolymer is according to formula II and has the CTFA designation "Poloxamine".

II:

$$(HO(CH_2CH_2O)_a(CHCH_2O)_b)_2—N—CH_2—CH_2—N—((OCH_2CH)_b(OCH_2CH_2)_aOH)_2$$
$$\quad\quad\quad\quad\quad\quad |\quad\quad\quad\quad\quad\quad\quad\quad\quad\quad\quad\quad\quad\quad\quad\quad |$$
$$\quad\quad\quad\quad\quad\quad CH_3\quad\quad\quad\quad\quad\quad\quad\quad\quad\quad\quad\quad\quad\quad\quad CH_3$$

Poloxamines are commercially available from BASF under the trade name "Tetronic". Suitably the mean value of a is 2 or more and the mean value of b is 2 or more.

Preferably, the mean value of a is 3 or more and the mean value of b is 3 or more. It is also preferred if the ratio a/b is from 0.1 to 15, more preferably from 0.5 to 6.

Suitably, the mean molecular weight of the poloxamine is 1000 unified atomic mass units or more, preferably 2000 or more, more preferably 4000 or more, most preferably 8000 or more.

The mean molecular weight is suitably measured by determining the hydroxyl number for the polymer then transforming this into molecular weight. This corresponds to a number based mean molecular weight.

In formula II, the degrees of polymerisation, a and b are indicated as the same for each polyethyleneoxide and polypropylene block respectively. For the sake of clarity, it should be explained that these degrees of polymerisation are mean values and are approximately the same rather than identical for any particular formula. This is a result of the polymerisation methods used for production of the compounds.

Suitably, the block copolymer is present in the composition at 0.01% or more by weight of the composition, preferably from 0.02% or more, more preferably 0.03%, most preferably 0.04% or more. Suitably, the block copolymer is present in the composition at 5% or less by weight of the composition, preferably at 2% or less, more preferably at 1% or less, most preferably at 0.6% or less. The most preferred level of block copolymer is from 0.05% to 0.3% by weight of the composition.

Hydrophobic Conditioning Oil

Compositions according to the invention comprise a water-insoluble hydrophobic conditioning oil. This may be a non-silicone hydrophobic oil but is more preferably a silicone conditioning agent. By water insoluble it is meant that the material has a solubility in water of 0.1% or less by weight of water at 25° C. Preferably the conditioning agent is non-volatile, meaning that it has a vapour pressure of less than 1000 Pa at 25° C. The conditioning oil is present in the composition as discrete emulsion droplets.

Emulsified hydrophobic conditioning oils for use in the shampoo or shower gel compositions of the invention suitably have an average droplet diameter ($D_{3,2}$) in the composition of 4 micrometers or less, preferably 2 micrometers or less, more preferably 1 micrometer or less.

A suitable method for measuring the $D_{3,2}$ mean diameter is by laser light scattering using an instrument such as a Malvern Mastersizer.

Silicone Conditioning Agents

The compositions of the invention can contain, emulsified droplets of a silicone conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the silicone itself (not the emulsion or the final hair conditioning composition) is typically from 350 to 200,000,000 $mm^2sec^{-1}$ at 25° C. Preferably the viscosity is at least 5,000 $mm^2sec^{-1}$ at 25° C., more preferably at least 10,000 $mm^2sec^{-1}$. Preferably the viscosity does not exceed 20,000,000 $mm^2sec^{-1}$, more preferably 10,000,000 $mm^2 sec^{-1}$, most preferably 5,000,000 $mm^2sec^{-1}$.

Viscosity of silicones can be measured using a glass capillary viscometer as set out in Dow Corning corporate test method CTM004 Jul. 20, 1970 at 25° C. Viscosities are generally provided by suppliers of silicones, either as measured or as dedeuced from their molecular weight.

It is preferred if the silicone oil also comprises a functionalised silicone. Suitable functionalised silicones include, amino-, carboxy-, betaine-, quaternary ammonium-, carbohydrate-, hydroxy- and alkoxy-substituted silicones.

Preferably, the functionalised silicone contains multiple substitutions.

For the avoidance of doubt, as regards hydroxyl-substituted silicones, a polydimethylsiloxane merely having hydroxyl end groups (which have the CTFA designation dimethiconol) is not considered a functionalised silicone within the definition of the present invention. However, a polydimethylsiloxane having hydroxyl substitutions along the polymer chain is considered a functionalised silicone.

A preferred class of functionalised silicone for inclusion in compositions of the invention is amino functional silicone. By "amino functional silicone" is meant a silicone containing at least one primary, secondary or tertiary amine group, or a quaternary ammonium group. Examples of suitable amino functional silicones include: polysiloxanes having the CTFA designation "amodimethicone", Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones). Suitable quaternary silicone polymers are described in EP-A-0 530 974. A preferred quaternary silicone polymer is K3474, ex Goldschmidt.

Another preferred functional silicone for use as a component in the hydrophobic conditioning oil is an alkoxy-substituted silicone. Such molecules are known as silicone copolyols and have one or more polyethyleneoxide or polypropyleneoxide groups bonded to the silicone polymer backbone, optionally through an alkyl linking group.

An example of a type of silicone copolyol useful in compositions of the invention has a molecular structure according to the formula depicted below:

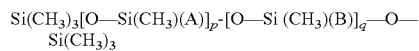

In this formula, A is an alkylene chain with from 1 to 22 carbon atoms, preferably 4 to 18, more preferably 10 to 16. B is a group with the structure: —(R)-(EO)$_r$(PO)$_s$—OH wherein R is a linking group, preferably an alkylene group with 1 to 3 carbon atoms. Preferably R is —(CH$_2$)$_2$—. The mean values of r and s are 5 or more, preferably 10 or more, more preferably 15 or more. It is preferred if the mean values of r and s are 100 or less. In the formula, the value of p is suitably 10 or more, preferably 20 or more, more preferably 50 or more and most preferably 100 or more. The value of q is suitably from 1 to 20 wherein the ratio p/q is preferably 10 or more, more preferably 20 or more. The value of p+q is a number from 11 to 500, preferably from 50 to 300.

Suitable silicone copolyols have an HLB of 10 or less, preferably 7 or less, more preferably 4 or less. A suitable silicone copolyol material is DC5200, known as Lauryl PEG/PPG-18/18 methicone (INCI name), available from Dow Corning.

Hydrophile/Lipophile balance or HLB is a well known parameter used by those skilled in the art to characterise surface active molecules and emulsifiers. Suitable methods for the experimental determination of HLB are in Griffin W. C, Journal of the Society of Cosmetic Chemists, volume 1 page 311 (1949). The commercially available silicone copolyols are supplied along with a value of their HLB by Dow Corning.

It is preferred to use a combination of amino and non functional silicones.

The total amount of silicone is preferably from 0.01% to 10% by weight of the total composition more preferably from 0.1% to 5%, most preferably 0.5% to 3%.

The silicones may be added to the composition as a fluid and subsequently emulsified, but preferably are added as pre-formed emulsions for ease of processing. Preferably, the pre-formed silicone emulsions additionally comprise a suitable emulsifier such as dodecylbenzenesulphonic acid, or are emulsified using the surface active block copolymer as the emulsifier.

Non-Silicone Hydrophobic Conditioning Oil

Compositions according to the present invention may comprise a dispersed, non-volatile, water-insoluble oily non-silicone conditioning agent.

Suitable oily or fatty materials are selected from hydrocarbon oils, fatty esters and mixtures thereof.

Straight chain hydrocarbon oils will preferably contain from about 12 to about 30 carbon atoms. Also suitable are polymeric hydrocarbons of alkenyl monomers, such as C2-C6 alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Another suitable material is polyisobutylene.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as C1-C22 carboxylic acids. Preferred materials include cocoa butter, palm stearin, sunflower oil, soyabean oil and coconut oil.

Preferably, the viscosity of the conditioning oil itself (not the emulsion or the final hair conditioning composition) is from 350 to 10,000,000 mm$^2$ sec$^{-1}$ at 25° C. More preferably the viscosity is at least 5,000 mm$^2$sec$^{-1}$ at 25° C., most preferably at least 10,000 mm$^2$sec$^{-1}$. Preferably the viscosity does not exceed 500,000 mm$^2$sec$^{-1}$.

The oily or fatty material is suitably present at a level of from 0.05 to 20, preferably from 0.2 to 10, more preferably from about 0.5 to 5 percent by weight of the composition.

Cationic Deposition Polymer

A cationic polymer is an essential ingredient in shampoo compositions of the invention, for enhancing conditioning performance of the shampoo.

The cationic polymer may be a homopolymer or be formed from two or more types of monomers. The molecular weight of the polymer will generally be between 5 000 and 10 000 000 Dalton, typically at least 10 000 and preferably from 100 000 to 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and copolymers of unsaturated carboxylic acids having from 3 to 5 carbon atoms, (as described in U.S. Pat. No. 4,009,256);

cationic polyacrylamides (as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density from 0.1 to 4 meq/g.

Cationic polysaccharide polymers suitable for use in compositions of the invention include those of the formula:

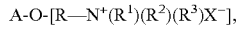

A-O-[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms.

The total number of carbon atoms for each cationic moiety (i.e., the sum of carbon atoms in R$^1$, R$^2$ and R$^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives.

Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.02 to 1, more preferably from 0.04 to 0.5 percent by weight of the composition.

Cleansing Surfactant

Such a shampoo composition will comprise one or more cleansing surfactants which are cosmetically acceptable and suitable for topical application to the hair. Further surfactants may be present as an additional ingredient if sufficient for cleansing purposes is not provided by the emulsifier for the water-insoluble oily component. It is preferred that shampoo compositions of the invention comprise at least one further surfactant (in addition to that used as emulsifying agent for the water-insoluble oily component) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n is from 1 to 3), ammonium lauryl sulphate and ammonium lauryl ether sulphate(n)EO, (where n is from 1 to 3).

Mixtures of any of the foregoing anionic cleansing surfactants may also be suitable.

The total amount of anionic cleansing surfactant in shampoo compositions of the invention is generally from generally from 0.5 to 45, preferably from 1.5 to 35, more preferably from 5 to 20 percent by weight of the composition.

Co-Surfactant

The composition can include co-surfactants, to help impart aesthetic, physical or cleansing properties to the composition.

A preferred example is an amphoteric or zwitterionic surfactant, which can be included in an amount ranging from 0 to about 8, preferably from 1 to 4 percent by weight of the composition.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms: Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 percent by weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The composition according to the invention can also optionally include one or more cationic co-surfactants included in an amount ranging from 0.01 to 10, more preferably from 0.05 to 5, most preferably from 0.05 to 2 percent by weight of the composition.

The total amount of surfactant (including any co-surfactant, and/or any emulsifier) in compositions of the invention is generally from 1 to 50, preferably from 2 to 40, more preferably from 10 to 25 percent by weight of composition.

A preferred blend of cleansing surfactants is a combination of ammonium lauryl ether sulphate, ammonium lauryl sulphate, PEG 5 cocamide and cocamide MEA (CTFA designations).

Suspending Agents

Optionally, the compositions according to the invention further comprise from 0.1 to 10 percent by weight, preferably from 0.6% to 6%, of a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Adjuvants

The compositions of the present invention may also contain adjuvants suitable for hair care. Generally such ingredients are included individually at a level of up to 2 percent by weight of the total composition.

Among suitable hair care adjuvants, are natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine. Another suitable adjuvant is glycolic acid.

Mode of Use

The compositions of the invention are primarily intended for topical application to the hair and/or scalp of a human subject in rinse-off compositions, in order to provide cleansing while improving hair fibre surface properties such as smoothness, softness, manageability, cuticle integrity, and shine.

The invention is further demonstrated with reference to the following, non-limiting examples:

EXAMPLES

TABLE 1

| Trade name | Chemical name | Supplier | Example A |
|---|---|---|---|
| Empicol ESB | Sodium Lauryl Ether Sulphate 2EO | Albright & Wilson | 16.0 |
| Tegobetaine CK | Cocoamidopropyl betaine | Goldschmidt | 2.0 |
| Carbopol 980 | Polyacrylate | Goodrich | 0.2 |
| Jaguar C-13-S | Guar hydroxypropyl trimonium chloride | Meyhall | 0.2 |
| DC-1785 | Silicone oil (as 100% oil) | Dow Corning | 2.0 |
| Euperlan PK300AM | Ethylene Glycol Distearate/laureth-4/CAPB | Cognis | 0.2 |
| Fragrance | Fragrance | IFF | 0.4 |
| Formaldehyde solution | Preservative | Sigma | 0.1 |
| Sodium Chloride | Viscosity builder | BDH | q.s. |
| Water | | | To 100% |

Example A, a comparative example was made up according to the formulation in table 1. DC 1785 is a commercial silicone from Dow Corning.

The formulation was prepared as follows. Water, formalin solution and sodium lauryl ether sulphate were mixed into a homogeneous solution. The Jaguar C13 was pre-dispersed in the fragrance then added to the homogeneous solution. Carbopol 980 was then added and fully dispersed, followed by the cocoamidopropyl betaine. The silicone was added as a pre-formed aqueous emulsion with 60% by weight of silicone oil. Euperlan PK300AM was then added with stirring for 10 minutes. The pH was adjusted to between 5.5 and 6.0 using NaOH solution, then NaCl was added to adjust the viscosity to approximately 4000 mm$^2$sec$^{-1}$. All operations were carried out at ambient (25° C.).

Examples B and examples 1 to 13 as shown in table 2 were prepared as for example A, but with 3% by weight of Poloxamer (based on the weight of emulsion) added to the silicone emulsion prior to blending into the formulation. This means that Examples B and 1 to 13 contain 0.1% by weight of the composition of Poloxamer.

For the Examples A,B and 1 to 13, selectivity was measured as follows.

0.25 g/5 cm switches of tip hair which had been cleaned with a solution of 14% SLES 2EO and 2% cocoamidopropyl betaine in water followed by extensive rinsing, were used for this experiment. The test shampoo was diluted to 1 in 10 by weight with distilled water and stirred throughout with a magnetic stirrer. 5 switches were placed in one half of a petri dish. 1.5 mls of diluted shampoo was placed along the length of the switches which were then agitated in the dish for 30 seconds, followed by a rinse for 30 seconds under tap water (12° French hard) at 40° C., with a flow rate set at 3-4 liters per minute. The washing process using the test shampoo solution was repeated followed again by rinsing. The switches were then allowed to dry naturally at 25° C. and a relative humidity of 45 to 60%.

The same sequence of experimentation was carried out for 0.25 g/5 cm samples of root hair.

The amount of silicone deposited on the hair samples was measured using X-ray fluorescence spectrometry (measured in parts per million (ppm) of silicon). The absolute selectivity is the ratio of silicon ppm on the tip samples to silicon ppm on the root samples. The relative selectivity, expressed as a percentage, is obtained by ratioing the absolute selectivity for each example to the absolute selectivity for example A.

TABLE 2

| Example | Poloxamer code name (ex BASF) | Relative Selectivity (%) | PO units in Poloxamer | EO units in Poloxamer |
|---|---|---|---|---|
| A | None | 100 | none | none |
| B | F127 | 101 | 69 | 99 |
| 1 | L31 | 161 | 16 | 1 |
| 2 | L62 | 136 | 30 | 2 |
| 3 | P103 | 128 | 56 | 17 |
| 4 | L44 | 124 | 21 | 10 |
| 5 | L64 | 129 | 30 | 13 |
| 6 | P84 | 138 | 39 | 19 |
| 7 | P85 | 114 | 39 | 26 |
| 8 | L35 | 133 | 16 | 11 |
| 9 | F77 | 125 | 35 | 52 |
| 10 | F108 | 105 | 56 | 132 |
| 11 | F98 | 122 | 47 | 123 |
| 12 | F68 | 122 | 30 | 76 |
| 13 | F38 | 131 | 16 | 42 |

Examples 14 to 18 as shown in table 3 were prepared as for example A, but with 3% by weight of Poloxamine (based on the weight of emulsion) added to the silicone emulsion prior to blending into the formulation. This means that Examples 14 to 18 contain 0.1% by weight of the composition of Poloxamine. Selectivity compared to Example A was measured as detailed above.

TABLE 3

| Example | Poloxamine code name (ex BASF) Tetronic | Relative Selectivity (%) | Molecular Weight of Poloxamine |
|---|---|---|---|
| 14 | 304 | 122 | 1650 |
| 15 | 704 | 134 | 5500 |
| 16 | 904 | 161 | 6700 |
| 17 | 908 | 196 | 25000 |
| 18 | 1307 | 207 | 18000 |

The invention claimed is:

1. A rinse off, aqueous hair conditioner composition comprising:
   a) discrete, dispersed droplets of a hydrophobic silicone conditioning oil with a mean diameter ($D_{3,2}$) of 4 micrometers or less,
   b) from 0.01 to 5% by weight of a cationic deposition polymer and
   c) 0.04% to 1% by weight of a block copolymer, comprising polyethyleneoxide and polypropyleneoxide blocks, selected from the group consisting of:
   (i) poloxamers according to formula I:

I:
   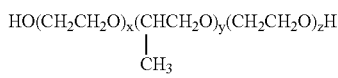

wherein said poloxamers are selected from the group consisting of:
      (ia) poloxamers according to formula I wherein the mean value of y is from 10 to 60 and the mean values of x and z are both from 1 to 20, and
      (ib) poloxamers according to formula I wherein the mean value of y is 35 and the mean values of x and z are both 52, and
   (ii) poloxamines according to formula II:

II:
   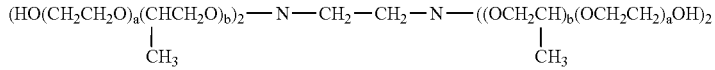

wherein the mean value of a is 2 or more and the mean value of b is 2 or more,
   d) from 5 to 20% by weight of the hair conditioning composition of anionic cleansing surfactant;
   e) co-surfactant; and
   f) optionally, emulsifier;
   wherein:
   (A) the rinse off aqueous hair conditioner composition is in the form of a shampoo,
   (B) the hydrophobic silicone conditioning oil is added to the composition as a pre-formed aqueous emulsion that includes the block copolymer, and
   (C) the total amount of surfactant, including any co-surfactant and emulsifier, is from 10 to 25 percent by weight of the composition.

2. A composition according to claim 1 wherein the value of y is 40 or less.

3. A composition according to claim 1 wherein the hydrophobic silicone conditioning oil comprises a functionalised silicone.

4. A composition according to claim 3, wherein the functionalised silicone is an amino-functionalised silicone.

5. A composition according to claim 1 wherein the mean diameter of the droplets of hydrophobic silicone conditioning oil ($D_{3,2}$) is 1 micrometer or less.

6. A composition according to claim 1 wherein the cationic deposition polymer is a cationic derivative of guar gum.

7. A method of selectively conditioning hair at the tips thereof, the method comprising the steps of:
   a) washing the hair with an aqueous hair conditioning composition according to claim 1, and
   b) rinsing the hair.

8. A composition according to claim 1 wherein the block copolymer comprises a poloxamine having a mean molecular weight of 4000 or more unified atomic mass units.

9. A composition according to claim 1 wherein the block copolymer comprises a poloxamine having a mean molecular weight of 6700 or more unified atomic mass units.

10. A composition according to claim 1 wherein the block copolymer comprises a poloxamine having a mean molecular weight of 8000 or more unified atomic mass units.

11. A composition according to claim 1 wherein the co-surfactant is selected from alkyl betaines, alkyl amidopropyl betaines and alkylsulphobetaines.

12. A composition according to claim 1 wherein the co-surfactant comprises cocamidopropyl betaine.

13. A composition according to claim 1 wherein the co-surfactant comprises a mono- or dialkyl alkanolamide co-surfactant.

14. A composition according to claim 1 wherein the block copolymer is present in an amount of 0.04 to 0.6% by weight of the composition.

15. A composition according to claim 1 wherein the block copolymer is present in an amount of 0.05 to 0.3% by weight of the composition.

16. A composition according to claim 1 wherein the mean value of y is from 10 to 40.

17. A composition according to claim 1 wherein the co-surfactant comprises at least one amphoteric or zwitterionic surfactant.

18. A composition according to claim 1 wherein the block copolymer is present in an amount of 0.04 to 0.6% by weight of the composition.

19. A rinse off, aqueous hair conditioner composition comprising:
   a) discrete, dispersed droplets of a hydrophobic silicone conditioning oil with a mean diameter ($D_{3,2}$) of 4 micrometers or less,
   b) from 0.01 to 5% by weight of a cationic deposition polymer,
   c) 0.04% to 0.6% by weight of a block copolymer, comprising polyethyleneoxide and polypropyleneoxide blocks, selected from the group consisting of:
   (i) poloxamers according to formula I:

I:
   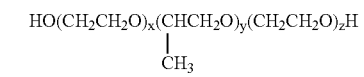

wherein the mean value of y is from 10 to 60 and the mean values of x and z are both from 1 to 150, and (ii) poloxamines according to formula II:

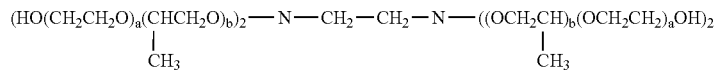

wherein the mean value of a is 2 or more and the mean value of b is 2 or more,
- d) from 5 to 20% by weight of the hair conditioning composition of anionic cleansing surfactant;
- e) co-surfactant; and
- f) optionally, emulsifier;

wherein:
- (A) the rinse off aqueous hair conditioner composition is in the form of a shampoo,
- (B) the hydrophobic silicone conditioning oil is added to the composition as a preformed aqueous emulsion that includes the block copolymer, and
- (C) the total amount of surfactant, including any co-surfactant and emulsifier, is from 10 to 25 percent by weight of the composition.

20. A composition according to claim 1 wherein the anionic cleansing surfactant is selected from the group consisting of alkyl sulphates, alkyl ether sulphates, alkaryl sulphonates, alkyl succinates, alkyl sulphosuccinates, alkyl phosphates, alkyl ether phosphates, alkyl ether carboxylates, the sodium magnesium, ammonium and mono-di, and tri-ethanolamines salts thereof, and mixtures thereof, wherein the alkyl groups of such surfactants contain from 8 to 18 carbon atoms and may be unsaturated and wherein the alkyl ether sulphates, alkyl ether phosphates and alkyl ether carbonates may contain from 1 to 10 ethylene oxide or propylene oxide units per molecule.

* * * * *